(12) United States Patent
Radocy

(10) Patent No.: US 9,034,047 B2
(45) Date of Patent: May 19, 2015

(54) ENERGY CAPTURING AND CONTROLLING JOINT MODULE FOR EXTERNAL PROSTHETICS

(76) Inventor: Robert Radocy, Boulder, CO (US)

(*) Notice: Subject to any disclaimer, the term of this patent is extended or adjusted under 35 U.S.C. 154(b) by 0 days.

(21) Appl. No.: 13/195,827

(22) Filed: Aug. 1, 2011

(65) Prior Publication Data

US 2014/0018926 A1    Jan. 16, 2014

Related U.S. Application Data

(60) Provisional application No. 61/369,554, filed on Jul. 30, 2010.

(51) Int. Cl.
| | | |
|---|---|---|
| *A61F 2/68* | (2006.01) | |
| *A61F 2/58* | (2006.01) | |
| *A61F 2/64* | (2006.01) | |
| *A61F 2/54* | (2006.01) | |
| *A61F 2/76* | (2006.01) | |
| *A61F 2/50* | (2006.01) | |

(52) U.S. Cl.
CPC ........... *A61F 2/64* (2013.01); *A61F 2002/6854* (2013.01); *A61F 2/582* (2013.01); *A61F 2/76* (2013.01); *A61F 2002/5003* (2013.01); *A61F 2002/5007* (2013.01); *A61F 2002/503* (2013.01)

(58) Field of Classification Search
CPC ................ A61F 2002/5003; A61F 2002/5007; A61F 2002/503; A61F 2/76; A61F 2002/6854
USPC ....................................................... 623/39, 59
See application file for complete search history.

(56) References Cited

U.S. PATENT DOCUMENTS

| | | | | |
|---|---|---|---|---|
| 2,551,537 | A * | 5/1951 | Havens | 623/44 |
| 2,698,947 | A * | 1/1955 | Dumelin | 623/44 |
| 6,258,128 | B1 * | 7/2001 | Saito et al. | 623/39 |
| 7,819,926 | B1 * | 10/2010 | Longino | 623/47 |
| 2002/0147501 | A1 * | 10/2002 | Wilkinson et al. | 623/35 |

FOREIGN PATENT DOCUMENTS

| | | | |
|---|---|---|---|
| FR | 991927 A | * | 10/1951 |
| FR | 2244444 A1 | * | 4/1975 |
| WO | WO00/09046 | * | 2/2000 |

* cited by examiner

*Primary Examiner* — Marcia Watkins
(74) *Attorney, Agent, or Firm* — Craig R. Miles; CR Miles P.C.

(57) ABSTRACT

A prosthetic joint module to provide a variety of motions and functions similar to human joint systems during rigorous activities. The joint module includes a housing component attached to a proximal prosthetic device, an elastomeric polymer attached to the housing component and a yoke component attached to the elastomeric polymer and to a distal prosthetic device. The yoke component and distal prosthetic device are moved relative to the housing component and proximal prosthetic device causing the elastomeric polymer to distort. This distortion allows the joint module to flex, and absorb, capture, store and return the energy from the movement to of the yoke component.

7 Claims, 3 Drawing Sheets

ENERGY CAPTURING AND CONTROLLING JOINT MODULE FOR EXTERNAL PROSTHETICS

RELATED INVENTIONS

This application claims the benefit of provisional application Ser. No. 61/369,554, filed on Jul. 30, 2010.

FIELD OF THE INVENTION

The present invention relates to the field of joint mechanisms for prosthetic devices.

BACKGROUND OF THE INVENTION

Existing joint mechanism for prosthetic devices simply act as torsion spring-like devices. The movement is constrained in two dimensions and simply return the energy from the movement of the prosthetic device. The energy is not absorbed, stored and returned or dampened in any way. Sideways or yawing movement is not possible with these devices.

SUMMARY OF THE INVENTION

The present invention provides a joint module for use with prosthetic devices to allow movement of the prosthetic device similar to that of human joints, such as elbows or knees. The joint module of the present invention provides a joint module that is capable of flexing, absorbing, capturing, storing and returning externally and bio-mechanically generated energy. This allows the individual to perform in rigorous activities with a prosthesis. The joint module is designed to be used with existing prosthetic devices as well as future prosthetic devices, and in particular, those prosthetic devices using major joints, such as elbows, knees and other joints, that undergo rigorous activities.

In a preferred embodiment of the present invention, the joint module includes a housing component with a proximal prosthetic attachment mechanism. An elastomeric polymer is secured within the housing component. A yoke component is secured to the housing component with a distal prosthetic attachment mechanism. In use, the yoke component and distal prosthetic device are moved relative to the housing component and the proximal prosthetic device. The polymer is thus distorted to allow the movement while absorbing and storing the energy from the resistance of the distortion. The polymer may allow movement in vectors in three dimensions, not just rotational in two dimensions. The energy from the release of the distortion will return the yoke component and distal prosthetic to their original position.

These and other features of the present invention will be evident from the ensuing detailed description of preferred embodiments, from the drawings and from the claims.

DETAILED DESCRIPTION OF PREFERRED EMBODIMENTS

Figure 1:
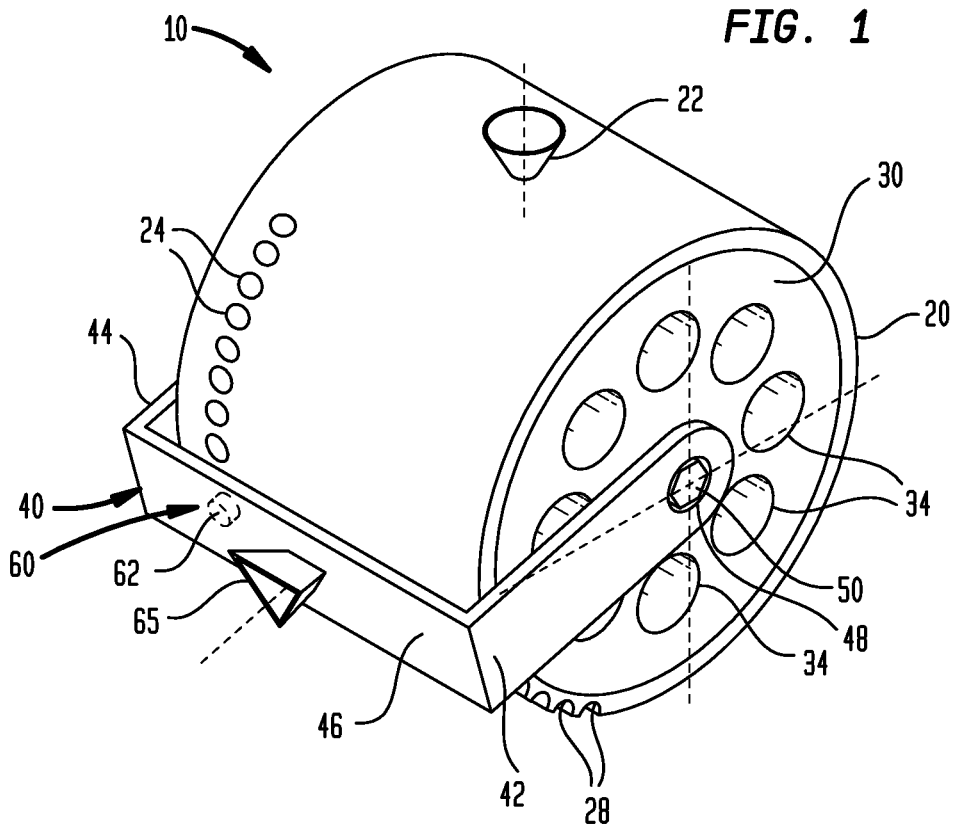
FIG. 1 illustrates a front perspective of a preferred embodiment of a joint module of the present invention.

The present invention provides a joint module for prosthesis that is able to emulate a variety of motions and functions in a manner similar to human joint systems. It is to be expressly understood that the present invention is not meant to be limited to the descriptive embodiments and encompasses other embodiments and alternatives.

The present invention in a preferred embodiment provides a joint module that is capable of flexing, absorbing, capturing, storing and returning externally and bio-mechanically generated energy. This allows the individual to perform in rigorous activities with a prosthesis. The joint module is designed to be used with existing prosthetic devices as well as future prosthetic devices, and in particular, those prosthetic devices using major joints, such as elbows, knees and other joints, that undergo rigorous activities.

In one preferred embodiment of the present invention, as shown in FIGS. 1-10, the joint module 10 includes a hard shell housing component 20, flexible elastomer polymer 30, and yoke component 40. In this preferred embodiment, the housing component 20 is a hollow cylindrical housing, although other shapes may be used as well. The housing component 20 also includes an attachment mechanism 22 for attaching the module to a prosthetic (not shown). The housing component also includes a series of positioning holes 24, or in the embodiment of FIG. 2, a series of notches 28 formed along an edge 26 of the housing component 20.

A flexible elastomer polymer 30 is mounted within the housing component 20. The polymer 30 is securely attached to the inner surface of the housing component 20 so that it will not slip relative to the housing component 20. Preferably, the housing 20 is filled and bonded with a matrix of elastomer materials. The polymer 30 includes a central axis hole 32 extending transversely through the polymer. A hollow core, sleeve or bushing is also attached within the central axis hole so that will not move relative to the polymer. In this preferred embodiment, the polymer 30 also includes a number of cavities or holes 34 extending transversely through the polymer as well. The size and the number of holes 34 is dependent upon the polymer property characteristics as well as the desired flexing, absorbing, capturing, storing and return of the joint module, as discussed in greater detail below.

Yoke component 40 includes parallel radial arms 42, 44 and outer member 46 connecting the radial arms. An axle shaft 50 extends through center holes 48 of radial arms 42, 44 and through center axis hole 32 of the polymer 30. The axle shaft 50 is mounted so that it will not rotate relative to the yoke component 40 or the polymer 30. Prosthetic attachment mechanism 65 is formed or mounted on the outer member 46 to attach the joint module to the distal prosthetic device. The distal prosthetic device could be an artificial hand, terminal device, foot or limb element or other device.

Figure 2:
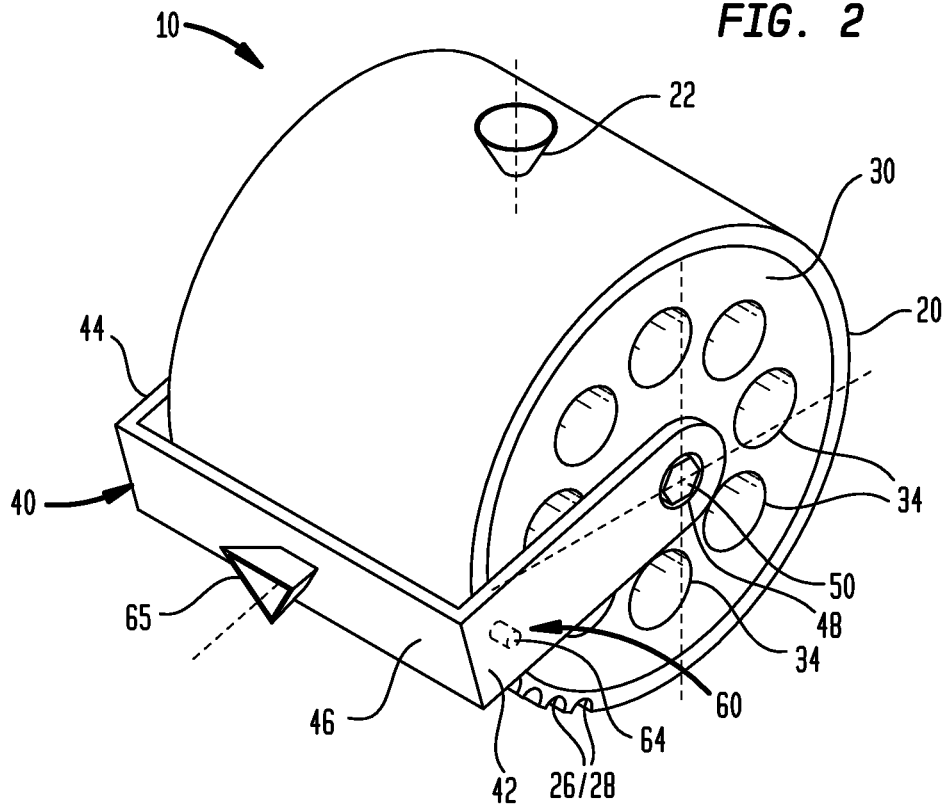
FIG. 2 illustrates the embodiment of FIG. 1 with a different position locking mechanism.

Position locking mechanism 60 allows the yoke component 40 to be adjustable positioned relative to the housing component 20 and the polymer 30 and locked in position so that the yoke component cannot then rotate relative to the housing component 20. The position locking mechanism 60 can include numerous embodiments, such as the pin locking mechanism 62 as shown in FIG. 1 that engages in the positioning holes 24 at the desired orientation, or the pin locking mechanism 64 as shown in FIG. 2 that engages in the notches 28 at the desired orientation. Other position locking mechanisms may be used as well.

In Use

Figure 3:
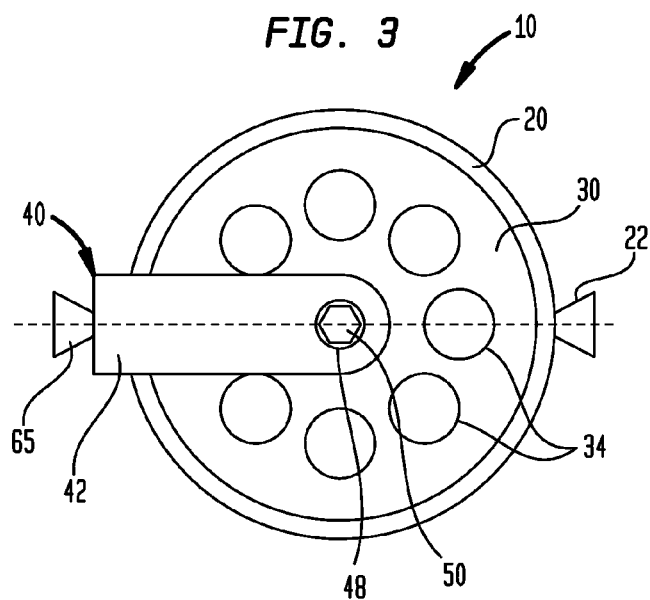
FIG. 3 illustrates a side view of the embodiment of FIG. 1 in a static position.
Figure 4:
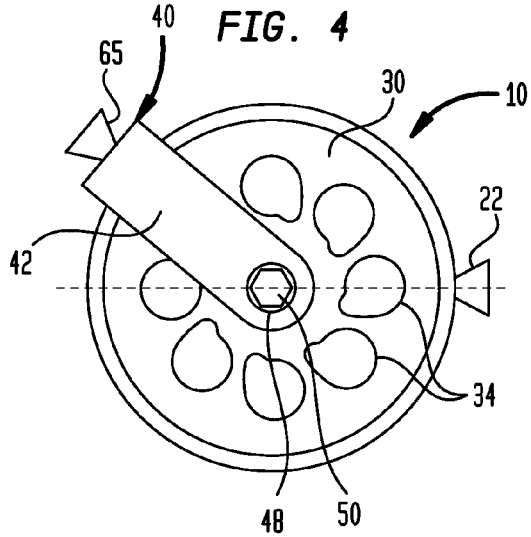
FIG. 4 illustrates the side view of the embodiment of FIG. 1 in a moving or loaded position.
Figure 5:
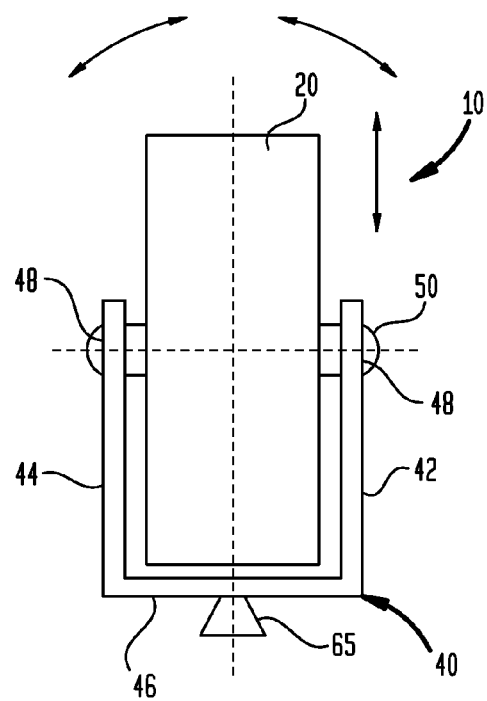
FIG. 5 illustrates a front view of the embodiment of FIG. 1 demonstrating rotation and side to side torque and compression.
Figure 6:
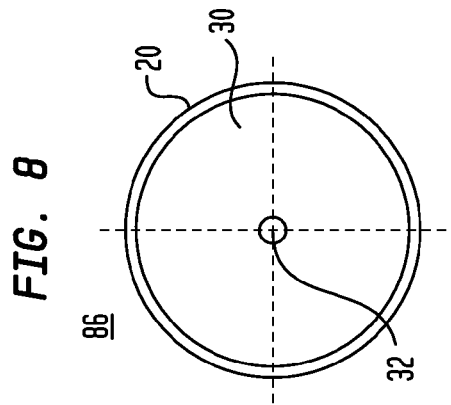
FIG. 6 illustrates a cross-sectional view of a different embodiment of the polymer.
Figure 7:
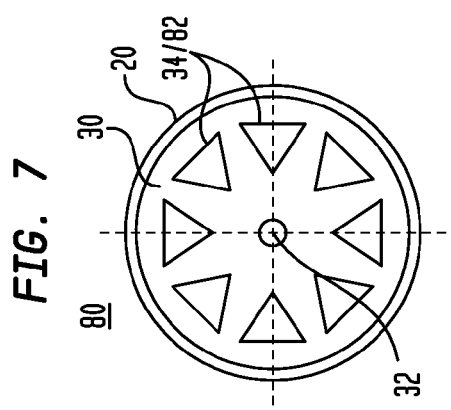
FIG. 7 illustrates a cross-sectional view of a different embodiment of the polymer.

As shown in FIGS. 3 and 4, the joint module 10 is initially in a static or at rest position with no load on the joint module. The desired orientation of the yoke component 40 (and prosthetic attachment) is selected relative to the housing component 20 and polymer component 30. The yoke component is then locked into position so that it can not freely rotate relative to the housing component 20. A load is then applied to the yoke component 40, as shown in FIG. 4, causing the yoke component to rotate relative to the housing component and proximal prosthetic of the individual. This rotation also causes the polymer 30 to distort relative to the housing compartment. This distortion not only allows the yoke component (and distal prosthetic device) to move relative to the housing component and limb, but also causes the polymer 30 to capture and store energy, similar to a torsion spring. The polymer can distort and flow material into the holes and cavities as well as flex outward and inward relative to the housing. In this embodiment, however, the polymer is able to create varying elastomeric resistance action in all the possible vectors within a three dimensional coordinate system, such as, but not limited to compression, flexion, torque, yaw, rotation and torsion spring-like resistances and actions. The energy can then be released to return the yoke component and distal prosthetic to its original position. The movement of the distal prosthetic can thus be in any vector or combination of vectors in three dimensional coordinates.

The joint module 10 can also be preloaded if desired by rotating the yoke component relative to the housing and then locking it place by the position locking mechanism. The energy can then be released by releasing the position locking mechanism.

Alternative Embodiments

Figure 8:
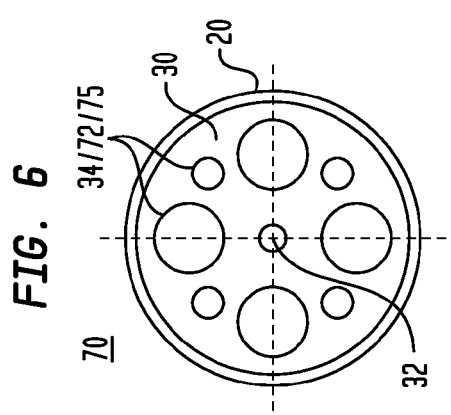
FIG. 8 illustrates a cross-sectional view of a different embodiment of the polymer.
Figure 9:
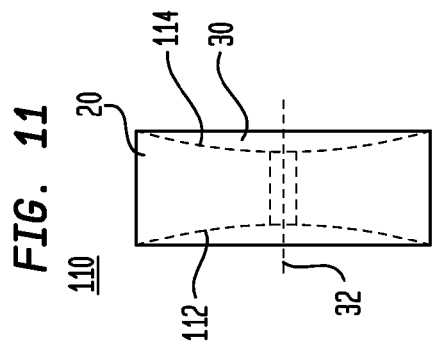
FIG. 9 illustrates a cross-sectional view of a different embodiment of the polymer.
Figure 10:
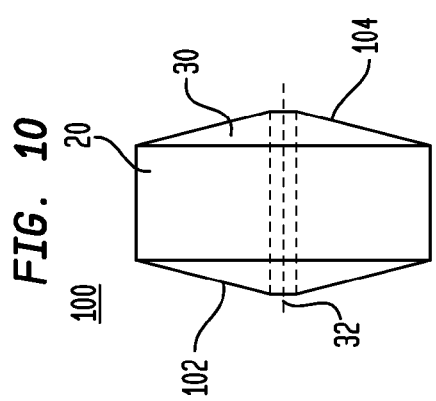
FIG. 10 illustrates a cross-sectional view of a different embodiment of the polymer.
Figure 11:
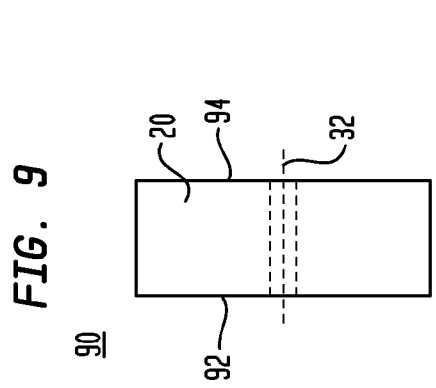
FIG. 11 illustrates a cross-sectional view of a different embodiment of the polymer.

The polymer 30 can be formed in any number of shapes and configurations. For example, as shown in embodiment 70 of FIG. 6, the polymer 30 may be cylindrical with differing sizes of transverse holes 72, 75 extending through it. The embodiment 80 of FIG. 7 has triangular shaped holes 82 extending through it. The embodiment 86 of FIG. 8 is solid with no transverse holes. The embodiment 90 of FIG. 9 is a cylindrical shape with parallel sides 92, 94. The embodiment 100 of FIG. 10 includes convex sides 102, 104. The embodiment 110 of FIG. 11 includes concave sides 112, 114. Each of these embodiments provide a joint module with different characteristics of movement, energy capture, storage and return depending on the shape and configuration of the polymer 30. Other embodiments may be used as well within the scope of the invention.

The polymer may also be formed on the exterior of the housing component in another embodiment. The attachment mechanisms on the yoke component and the housing component may also be reversed in another embodiment. It is to be expressly understood that the above description of preferred embodiments are intended for explanatory purposes only and are not meant to limit the scope of the claimed inventions.

What is claimed is:

1. A joint module for prosthetic devices, said joint module comprising:
   a hard shell housing component having an outer surface and an inner surface which defines an open space inside of said hard shell housing;
   an elastomeric component disposed within said open space and coupled to said inner surface of said hard shell housing component, said elastomeric component having a central axis hole and at least one transverse hole which extends axially between a pair of sides of said elastomeric component, said at least one transverse hole disposed a distance radially outward of said central axis hole;
   an axle shaft which extends through said central axis hole;
   a yoke including an outer member connecting a pair of radial arms, said pair of radial arms correspondingly directly connected to opposed ends of said axle shaft extending though said central axis hole, said elastomeric component coupled to said axle shaft and disposed between said pair of radial arms, whereby rotation of said yoke in relation to said hard shell housing distorts said elastomeric element;
   a locking mechanism directly coupling said hard shell housing and said yoke, said locking mechanism configured to prevent rotation of said yolk in relation to said hard shell housing;
   a proximal prosthetic attachment mechanism attached to said hard shell housing component; and
   a distal prosthetic attachment mechanism attached to said yoke component.

2. The joint module for prosthetic devices of claim 1, wherein said pair of sides of said elastomer component comprise parallel sides.

3. The joint module for prosthetic devices of claim 1, wherein said pair of sides of said elastomer component comprise convex sides.

4. The joint module for prosthetic devices of claim 1, wherein said pair of sides of said elastomer component comprise concave sides.

5. The joint module for prosthetic devices of claim 1, wherein said at least one transverse hole has a cylindrical configuration.

6. The joint module for prosthetic devices of claim 1, wherein said at least one transverse hole has a triangular configuration.

7. The joint module for prosthetic devices of claim 1, wherein said locking mechanism allows variable fixed positioning of said yolk in relation to said hard shell housing to variably tension said polymeric component.

* * * * *